US006258543B1

(12) United States Patent
Gerdes et al.

(10) Patent No.: US 6,258,543 B1
(45) Date of Patent: *Jul. 10, 2001

(54) QUANTITATION OF RNA TRANSCRIPTS USING GENOMIC DNA AS THE INTERNAL AMPLIFICATION COMPETITOR

(75) Inventors: John C. Gerdes, Denver; Jeffrey M. Marmaro, Aurora, both of CO (US)

(73) Assignee: Xtrana, Inc., Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/398,539

(22) Filed: Sep. 17, 1999

Related U.S. Application Data

(63) Continuation-in-part of application No. 08/850,613, filed on May 2, 1997, now Pat. No. 6,063,568.
(60) Provisional application No. 60/016,710, filed on May 2, 1996.

(51) Int. Cl.[7] .............................. C12Q 1/68; C12P 19/34; C07H 21/04
(52) U.S. Cl. .......................... 435/6; 435/91.2; 435/91.21; 435/91.51; 536/24.33
(58) Field of Search .......................... 435/6, 91.2, 91.21, 435/91.51; 536/24.33

(56) References Cited

U.S. PATENT DOCUMENTS 5,213,961 * 5/1993 Bunn et al. ............................... 435/6
5,876,978 * 3/1999 Willey et al. ........................ 435/91.2

OTHER PUBLICATIONS

Zenilman et al. Analytical Biochemistry. 224:339–346, 1995.*
Gotteland et al. Molecular and Cellular Endocrinology, 112:1–13, 1995.*

* cited by examiner

*Primary Examiner*—Carla J. Myers
(74) *Attorney, Agent, or Firm*—Steven C. Petersen; Sarah S. O'Rourke; Hogan & Hartson, LLP

(57) ABSTRACT

This invention is directed to methods for the quantitative measurement of specific gene expression levels in biological samples. In one embodiment, methods for the quantitative monitoring of gene expression without either co-amplification of an added template or use of an endogenous constitutive transcript are provided. The former involves a duplex amplification reaction in which a single set of primers is used to amplify both genomic DNA and expressed mRNA from the same gene sequence. These primers are targeted for sequences flanking the splice junction and intron sequences for the mRNA and DNA respectively. By their use, any suitable nucleic acid amplification technology yields mRNA and DNA amplimers which are distinguishable by length and sequence heterogeneity. These amplimers are also present in the final amplification reaction in ratios which are dependent upon the ratios of the expressed mRNA to the DNA in the sample, allowing the quantitation of mRNA in a sample which is normalized to the number of copies of genomic DNA since the genomic DNA acts as the internal quantitation standard, and in effect yields the amount of mRNA per cell. Any detection methodology which can detect amplimers of different lengths or sequences can be used for post amplification quantitation. This strategy may be employed for any gene system in which the mRNA sequence differs from the original genomic DNA sequence. In another embodiment, methods for the quantitative monitoring of gene expression involving determining the ratio of genomic material to expressed mRNA without nucleic acid amplification and/or primer binding are described. This method includes the independent and direct detection of the genomic material and mRNA by complementary probe binding without prior amplification. Additional methods for quantitative measurement of gene expression rates without RNA transcription region introns are described. The invention is useful in gene expression determination in research and commercial applications.

13 Claims, 8 Drawing Sheets

FIGURE 4: Agarose Gel Electrophoresis of 40-Cycle PCR amplification reactions. DNA copy number constant at 25 copies per reaction. Messenger RNA concentration varied from 5 to 5000 copies per reaction.

SEQUENCE LISTING

```
<160> NUMBER OF SEQ ID NOS: 17

<210> SEQ ID NO 1
<211> LENGTH: 17
<212> TYPE: DNA
<213> ORGANISM: Homo sapiens

<400> SEQUENCE: 1
gtcttgcatt gcactaa                                                   17

<210> SEQ ID NO 2
<211> LENGTH: 17
<212> TYPE: DNA
<213> ORGANISM: Homo sapiens

<400> SEQUENCE: 2
taaatgtgag catcctg                                                   17

<210> SEQ ID NO 3
<211> LENGTH: 29
<212> TYPE: DNA
<213> ORGANISM: Homo sapiens
<220> FEATURE:
<221> NAME/KEY: misc_feature
<222> LOCATION: (1)..()
<223> OTHER INFORMATION: Reporter coupled to the first nucleotide
<221> NAME/KEY: misc_feature
<222> LOCATION: (29)..()
<223> OTHER INFORMATION: Quencher coupled to the last nucleotide

<400> SEQUENCE: 3
ttgggattct tgtaattatt aattccatt                                      29

<210> SEQ ID NO 4
<211> LENGTH: 26
<212> TYPE: DNA
<213> ORGANISM: Homo sapiens
<220> FEATURE:
<221> NAME/KEY: misc_feature
<222> LOCATION: (1)..()
<223> OTHER INFORMATION: Reporter coupled to the first nucleotide
<221> NAME/KEY: misc_feature
<222> LOCATION: (26)..()
<223> OTHER INFORMATION: Quencher coupled to the last nucleotide

<400> SEQUENCE: 4
ttgcacttgt cacaaacagt gcacct                                         26

<210> SEQ ID NO 5
<211> LENGTH: 18
<212> TYPE: DNA
<213> ORGANISM: Homo sapiens

<400> SEQUENCE: 5
gttattgggc gcctggtc                                                  18

<210> SEQ ID NO 6
<211> LENGTH: 19
<212> TYPE: DNA
<213> ORGANISM: Homo sapiens

<400> SEQUENCE: 6
cgctcctgga agatggtga                                                 19
```

```
<210> SEQ ID NO 7
<211> LENGTH: 30
<212> TYPE: DNA
<213> ORGANISM: Homo sapiens
<220> FEATURE:
<221> NAME/KEY: misc_feature
<222> LOCATION: (1)..()
<223> OTHER INFORMATION: Reporter coupled to the first nucleotide
<221> NAME/KEY: misc_feature
<222> LOCATION: (30)..()
<223> OTHER INFORMATION: Quencher coupled to the last nucleotide

<400> SEQUENCE: 7
tgacctcaac tacatggttt acatgttcca                                    30

<210> SEQ ID NO 8
<211> LENGTH: 27
<212> TYPE: DNA
<213> ORGANISM: Homo sapiens
<220> FEATURE:
<221> NAME/KEY: misc_feature
<222> LOCATION: (1)..()
<223> OTHER INFORMATION: Reporter coupled to the first nucleotide
<221> NAME/KEY: misc_feature
<222> LOCATION: (27)..()
<223> OTHER INFORMATION: Quencher coupled to the last nucleotide

<400> SEQUENCE: 8
cagccccttc ataccctcac gtattcc                                       27

<210> SEQ ID NO 9
<211> LENGTH: 19
<212> TYPE: DNA
<213> ORGANISM: Homo sapiens

<400> SEQUENCE: 9
tggcgctgag tacgtcgtg                                                19

<210> SEQ ID NO 10
<211> LENGTH: 20
<212> TYPE: DNA
<213> ORGANISM: Homo sapiens

<400> SEQUENCE: 10
acatgggggc atcagcagag                                               20

<210> SEQ ID NO 11
<211> LENGTH: 24
<212> TYPE: DNA
<213> ORGANISM: Homo sapiens
<220> FEATURE:
<221> NAME/KEY: misc_feature
<222> LOCATION: (1)..()
<223> OTHER INFORMATION: Reporter coupled to the first nucleotide
<221> NAME/KEY: misc_feature
<222> LOCATION: (24)..()
<223> OTHER INFORMATION: Quencher coupled to the last nucleotide

<400> SEQUENCE: 11
atggagaagg ctggggctca tttg                                          24

<210> SEQ ID NO 12
<211> LENGTH: 24
<212> TYPE: DNA
<213> ORGANISM: Homo sapiens
<220> FEATURE:
<221> NAME/KEY: misc_feature
<222> LOCATION: (1)..()
<223> OTHER INFORMATION: Reporter coupled to the first nucleotide
```

```
<221> NAME/KEY: misc_feature
<222> LOCATION: (24)..()
<223> OTHER INFORMATION: Quencher coupled to the last nucleotide

<400> SEQUENCE: 12
agctgactca gccctgcaaa ggca                                              24

<210> SEQ ID NO 13
<211> LENGTH: 24
<212> TYPE: DNA
<213> ORGANISM: Homo sapiens
<220> FEATURE:
<221> NAME/KEY: misc_feature
<222> LOCATION: (1)..()
<223> OTHER INFORMATION: Reporter coupled to the first nucleotide
<221> NAME/KEY: misc_feature
<222> LOCATION: (24)..()
<223> OTHER INFORMATION: Quencher coupled to the last nucleotide

<400> SEQUENCE: 13
ttattaattc cattcaaaat catc                                              24

<210> SEQ ID NO 14
<211> LENGTH: 24
<212> TYPE: DNA
<213> ORGANISM: Homo sapiens
<220> FEATURE:
<221> NAME/KEY: misc_feature
<222> LOCATION: (1)..()
<223> OTHER INFORMATION: Reporter coupled to the first nucleotide
<221> NAME/KEY: misc_feature
<222> LOCATION: (24)..()
<223> OTHER INFORMATION: Quencher coupled to the last nucleotide

<400> SEQUENCE: 14
tgttattaag aaatgatctc cagc                                              24

<210> SEQ ID NO 15
<211> LENGTH: 21
<212> TYPE: DNA
<213> ORGANISM: Homo sapiens

<400> SEQUENCE: 15
cgccggtttc tgagccttct g                                                 21

<210> SEQ ID NO 16
<211> LENGTH: 21
<212> TYPE: DNA
<213> ORGANISM: Homo sapiens

<400> SEQUENCE: 16
tgctttggtg tggagggtca t                                                 21

<210> SEQ ID NO 17
<211> LENGTH: 21
<212> TYPE: DNA
<213> ORGANISM: Homo sapiens

<400> SEQUENCE: 17
gctgtctgtg gctggctgcg t                                                 21
```

QUANTITATION OF RNA TRANSCRIPTS USING GENOMIC DNA AS THE INTERNAL AMPLIFICATION COMPETITOR

RELATED APPLICATIONS

This application is a continuation-in-part of the application having U.S. Ser. No. 08/850,613, filed on May 2, 1997 now U.S. Pat. No. 6,063,568, which claims priority to provisional patent application serial no. 60/016,710, filed May 2, 1996, now abandoned. The earlier filing date of this application is hereby claimed.

FIELD OF INVENTION

This invention relates to the general fields of molecular biology, biochemistry, genetics and biological research, and specifically, relates to methods for the quantitative determination of relative amount and precise copy number of messenger RNA transcripts in biological samples. This method, thus, further relates to commercial applications in the areas of medical and biological research and medical diagnostics.

BACKGROUND AND PRIOR ART

Nucleic acid probe technology has been discovered for its value in the detection of various diseases, organisms or genetic defects, and thus, has developed quite rapidly. Current techniques provide the sensitivity lacking in earlier assays and necessary to qualitatively determine the presence of minute quantities of nucleic acid. That is, they are sensitive enough to be able to detect a single copy of a specific nucleic acid sequence. The use of nucleic acid probe tests based on hybridization for quantitative analysis is hindered by a lack of sensitivity.

A number of methodologies involving amplification of nucleic acids are currently used for the measurement of gene expression. The most sensitive of these methodologies utilizes the polymerase chain reaction (PCR) technique, the details of which are provided in U.S. Pat. No. 4,683,195, U.S. Pat. No. 4,683,202, and U.S. Pat. No. 4,965,188, all to Mullis et al., all of which are specifically incorporated herein by reference. The details of PCR technology, thus, are not included herein. Recently, additional technologies for the amplification of nucleic acids have been described, most of which are based upon isothermal amplification strategies as opposed to the temperature cycling required for PCR. These strategies include, for example, Strand Displacement Amplification (SDA)(U.S. Pat. Nos. 5,455,166 and 5,457,027 both to Walker; Walker et al. (1992) PNAS 89:392; each of which is specifically incorporated herein by reference) and Nucleic Acid Sequence-Based Amplification (NASBA)(U.S. Pat. No. 5,130,238 to Malek et al.; European Patent 525882 to Kievits et al.; both of which are specifically incorporated herein by reference). Each of these amplification technologies are similar in that they employ the use of short, deoxyribonucleic acid primers to define the region of amplification, regardless of the enzymes or specific conditions used.

Generally, amplification of DNA molecules utilizes a thermostable polymerase, for example, Taq polymerase, described in European Patent 258017, specifically which is incorporated herein by reference. Until recently, RNA amplification required a separate, additional step involving the use of non-thermostable reverse transcriptase enzymes to generate a cDNA capable of being amplified by a thermostable DNA polymerase, such as Taq. The discovery of a recombinant thermostable enzyme (rTth) capable of coupling reverse transcription of the RNA with DNA amplification in a single enzyme:single reaction procedure greatly simplified and enhanced RNA amplification (see, Myers & Gelfand (1991) Biochemistry 30:7661–7666; U.S. Pat. No. 5,407,800 to Gelfand and Myers, both of which are specifically incorporated herein by reference). Recombinant thermostable enzyme polymerase chain reaction (rTthPCR) is exquisitely sensitive.

All PCR-based methods for measuring gene expression have certain features in common: the nucleic acids from a chosen sample must be extracted, and, the target sequence is amplified by PCR, allowing detection and quantitation of that sequence. However, some notable difficulties are encountered when applying PCR to the quantitative measurement of gene expression. The efficiencies of both the extraction step and the amplification step directly affect the outcome of the assay. To determine the number of original copies, the efficiency of the nucleic acid extraction, as well as the efficiency of each PCR reaction must be known. Further, the detection step reveals how many copies of the target sequence have been made, but not how many copies were contained in the original sample An absolute quantitation of sample copy number is difficult using the current state of extraction technologies—if not impossible. The best that can be achieved on a routine basis is quantifying changes in gene expression rate, rather than quantifying the exact numbers of copies of the target sequence contained in the sample. However, this quantification of gene expression rate changes can only be done if the efficiencies of the extraction and amplification processes are constant or can be controlled. There are two basic types of control: the first is commonly known as exogenous control (Gilliland et al. (1990) PCR Protocols, Innis et al. ed., pp. 60–69, Academic Press; Wang et al. (1989) Proc. Natl. Acad. Sci. USA 86:9717–9721, both of which are specifically incorporated herein by reference), and the second, is known as endogenous control (Dveksler et al. (1992) PCR Methods and Applications 6:283–285; Spanakis (1993) Nucleic Acids Research 21:3809–3819, both of which are specifically incorporated herein by reference).

Exogenous control involves the use of an artificially introduced nucleic acid molecule that is added, either to the extraction step or to the PCR step, in a known concentration. The concept of adding an exogenous nucleic acid at a known concentration in order to act as an internal standard for quantitation was introduced by Chelly et al. (1988) Nature 333:858–860, which is specifically incorporated herein by reference. This approach was improved following the realization that PCR amplification efficiency is dependent upon the primer sequences (WO 91/02817 to Wang et al., which is specifically incorporated herein by reference). Therefore, utilizing a control fragment that is amplified with the same primers as the target sequence more accurately reflects target sequence amplification efficiency relative to the internal standard (see, for example, WO 93/02215 to Fox and Griffiths; WO 92/11273 to McCallum et al.; U.S. Pat. No. 5,213,961 to Bunn et al.; and, U.S. Pat. No. 5,219,727 to Wang et al., all of which are specifically incorporated herein by reference). Similar strategies have proven effective for quantitative measurement of nucleic acids utilizing isothermal amplification reactions such as NASBA (Kievits et al., supra) or SDA (Walker, supra).

The use of an endogenous control regulates variations in extraction efficiency. Control choice is important in that several requirements must be met in order for it to work. The first requirement is that the copy number of the control must remain constant; the second. Requirement is that the control must amplify with similar efficiency to the sequence being monitored. Several constitutively expressed genes have been considered as control candidates, since the expression of these genes is relatively constant over a variety of conditions. The most common of these are the β-actin gene, the glyceraldehyde-3-phosphate dehydrogenase gene (GAPDH), and the 16S ribosomal RNA gene. While these genes are considered to be constitutively expressed, they are not ideal for the above-discussed purpose. The first problem is that under some conditions the expression level of these genes varies (Spanakis (1993) supra; Dveksler et al. (1992) supra) possibly invalidating them as controls. Further, these genes necessitate using a different set of PCR primers from any other gene being assayed, possibly leading to differences in PCR efficiency, and thus, invalidating them as controls. Zenilman et al. ((1995) *Analytical Biochemistry* 224:339–346, which is specifically incorporated herein by reference) attempted to design a competitive polymerase chain reaction method that altered the cDNA generated during reverse transcription using a composite primer to introduce a common intron primer sequence into the cDNA, such that both genomic DNA and cDNA could then be amplified with the same primer set. That method requires careful design of the composite primers so that, following reverse transcription, the melting temperature (Tm) differential between the composite and DNA primers is adjusted to prevent the composite primer from binding to the genomic DNA. It further requires separate steps for reverse transcription and DNA amplification, and uses a cumbersome, impractical radioactive detection methodology.

The detection of amplified products following quantitative PCR must provide a method of distinguishing the added control standard from the target nucleic acid sequence. Endogenous controls include, for example, radioactive probes specific to the control sequence, wherein the control and target detection is split into separate detection reactions for each amplification tube. Exogenous standards have been designed so as to be distinguishable by the size of the amplimer as visualized on an agarose gel (Scadden et al. (1992) *J. Infect. Dis.* 165:1119–1123; Piatak et al. (1993) *Biotechniques* 14:70–80, both of which are specifically incorporated herein by reference) or by introducing an internal restriction site through mutagenesis, wherein the restriction fragments are again detected on an agarose gel (Becker-Andre and Hahlbrock (1989) *Nucleic Acid Res.* 17:9437–9446; Steiger et al. (1991) *J. Virol. methods* 34:149–160, both of which are specifically incorporated herein by reference). All of these methods employ a relatively insensitive and imprecise detection method. More recently developed methods utilize chemiluminescent or enzyme-linked immunosorbent assay (ELISA) based detection that more precisely measure amplified product (Mulder et al. (1994) *J. Clin. Microbiol.* 32:292–300, which is specifically incorporated herein by reference).

To overcome some of the shortcomings of the above described methodologies, detection methods involving a homogeneous assay, wherein detection occurs concomitantly with amplification are employed. This is possible utilizing the nuclease assay methodology described in U.S. Pat. No. 5,210,015 to Gelfand et al., which is specifically incorporated herein by reference. The preferred probes for the nuclease assay, that is those probes having the greatest specificity, are described by Livak et al. (U.S. Ser. No. 08/340,558, now U.S. Pat. No. 5,538,848; U.S. Ser. No. 08/559,405, now U.S. Pat. No. 5,723,591; and, U.S. Ser. No. 08/558,303, now U.S. Pat. No. 5,876,930 the specifications of which are specifically incorporated herein by reference). These preferred probes, designated TaqMan® probes and developed by the Perkin Elmer Corp. (Foster City, Calif.), utilize energy transfer fluorescence methods, wherein the probes are self-quenched until cleaved during the PCR nuclease assay. Cleavage during PCR generates an increased fluorescence signal. Furthermore, several reporter dyes can be monitored in the same reaction.

The characteristics of an ideal quantitation control include: presence in unchanging concentrations in the cell; PCR efficiencies equivalent to those of the system being assayed; and, high distinguishability from the system being assayed. It is further desirable that the control is a natural componenet of the biological specimen making it unnecessary to synthesize and externally add an artificial standard, and the control must accurately accommodate fluctuations both in nucleic acid extraction as well as amplification efficiencies. Finally, the control must be accurately distinguishable from the target, preferably by an homogeneous assay of such specificity so as to have no cross reactivity that alters the ratio of the two. The quantitation methodology disclosed herein meets these requirements by integrating existing technologies with novel amplification and primer design techniques, as disclosed herein.

SUMMARY OF THE INVENTION

This invention is based on a novel concept for quantitatively measuring the level of specific gene expression in biological samples. More specifically, methodologies are provided for the quantitative determination of RNA transcripts using genomic DNA as an internal amplification competitor and for the quantitative determination of RNA transcripts without nucleic acid amplification and/or primer binding. This invention is concerned primarily with a novel amplification-primer methodology useful for the quantitation of nucleic acid using any amplification method, including but not limited to the aforementioned strategies. In particular, this application describes a method for the quantitation of RNA transcripts using genomic DNA as an amplification competitor.

First disclosed is an amplification method using genomic DNA as the endogenous quantitation standard. Furthermore, the present invention encompasses a novel method for designing amplification primers such that they exploit sequence differences and/or length differences that occur with design strategies, and therefore, any method wherein primers are employed to define the amplification region may be used in concert herewith. In preferred embodiments, the instant invention methodology is defined by an extraction step, a designing step, a hybridization and amplification step and a determination step, and is applicable to all amplification methods, in which the amplification of both DNA and RNA is provided in a competitive reaction. Moreover, the present invention is applicable to any transcribed gene, wherein both the RNA and DNA sequences are characterized, but where there also exists some sequence heterogeneity between the RNA and DNA sequences.

Secondly, disclosed is a methodology for the independent detection of the genomic material and the mRNA by complementary probe binding, wherein the probe is directly detected without prior amplification of the genomic material and the mRNA.

The present invention is useful for reliable, quantitation of specific gene transcription—determining changes in ratios or copy numbers of RNA per cell—but is not intended to be limited to this use.

In an embodiment of this invention, a nucleic acid sample is obtained, primer and probe sequences designed, hybridization and amplification performed and relative gene expression determined by relative quantitation of RNA and DNA amplimers.

In another embodiment of this invention, genomic DNA and mRNA are amplified by a suitable amplification technique such as PCR using a single set of primers, said primers designed such that they are located complementary to sequences within two exons flanking an intron of a certain size, as dictated by the method of amplification, and, two fluorescently tagged probes ar also designed one of which specifically hybridized to the mRNA splice junction, and the other hybridizes to a sequence contained only in the intron of the same gene. For example, in certain methods of amplification, an intron that is too large in size compromises the amplification efficiency. This embodiment enables the application of the instant invention in such cases through the modification of primer design strategies. Gene expression is thus determined through multiplex componenting the ratio of RNA (splice junction probe) to DNA (intron probe) signals.

The invention described herein provides for a duplex amplification reaction allowing competitive PCR quantitation. PCR primers are designed to be complementary to sequences within two exons flanking an intron and facilitate DNA and RNA being amplified by PCR using a single set of primers. The DNA amplimer is longer than the mRNA amplimey by the length of the intron. The DNA amplimer is further distinguishable from the mRNA amplimer by sequence heterogeneity. That is, the DNA amplimer contains the intron sequence, while the RNA amplimer does not. The mRNA amplimer contains the continuous splice junction sequence, while the DNA amplimer does not. The PCR products of the DNA are thus distinguishable from those of the RNA by any method that capitalizes on the above-described differences. For example, by using "TaqMan®" (5'-nuclease) probes in which one probe with a certain reporter dye binds to an intron sequence and another with a different reporter dye binds to the splice junction sequence in a PCR amplification reaction, the ratios of DNA amplimer to RNA amplimer are determined. The sequence specificity of these TaqMan® probes prohibits signal cross-talk between DNA and RNA amplimer measurements. Thus, the ratio of the mRNA signal to that of the DNA signal accurately reflects the ratio of mRNA to DNA in the original sample. This method of measurement can be applied to accurately and conveniently monitor changes in gene expression independent of extraction and amplification efficiency, since DNA signal always serves as the endogenous quantitation standard.

Another embodiment includes the assay for gene expression using the ratio of genomic material to expressed mRNA as measured by any complementary DNA, RNA or PNA (protein nucleic acid) probe binding to the genomic material and mRNA, and further, discriminating between the genomic material and mRNA by sequence heterogeneity without nucleic acid amplification and/or primer binding.

Another embodiment of this invention provides for quantitative measurement of gene expression without RNA transcription region introns, wherein primers complementary to sequences in the transcription region amplify both the RNA and DNA materials.

The instant invention also relates generally to quantitative gene expression determination. This invention may, but does not necessarily, rely upon principles of hybridization primer based nucleic acid amplification, including, for example, PCR, SDA and NASBA. The process and method according to the present invention is suitable for the quantitation of all characterized genes for which some degree of mRNA processing results in sequence heterogeneity between the DNA and the mRNA, such as intron excision and splicing. The sensitivity and accuracy of the methods disclosed herein are improved in relation to current technologies, offering the possibility of simplicity, reliability and specificity.

Other features and advantages of the instant invention will become apparent from the following detailed description, taken in conjunction with the accompanying figures, that illustrate by way of example, the principles of the instant invention.

DETAILED DESCRIPTION OF THE PREFERRED EMBODIMENT

It is to be understood that both the foregoing general description and the following detailed description are exemplary and explanatory only and are not restrictive of the invention as claimed.

Figure 1:
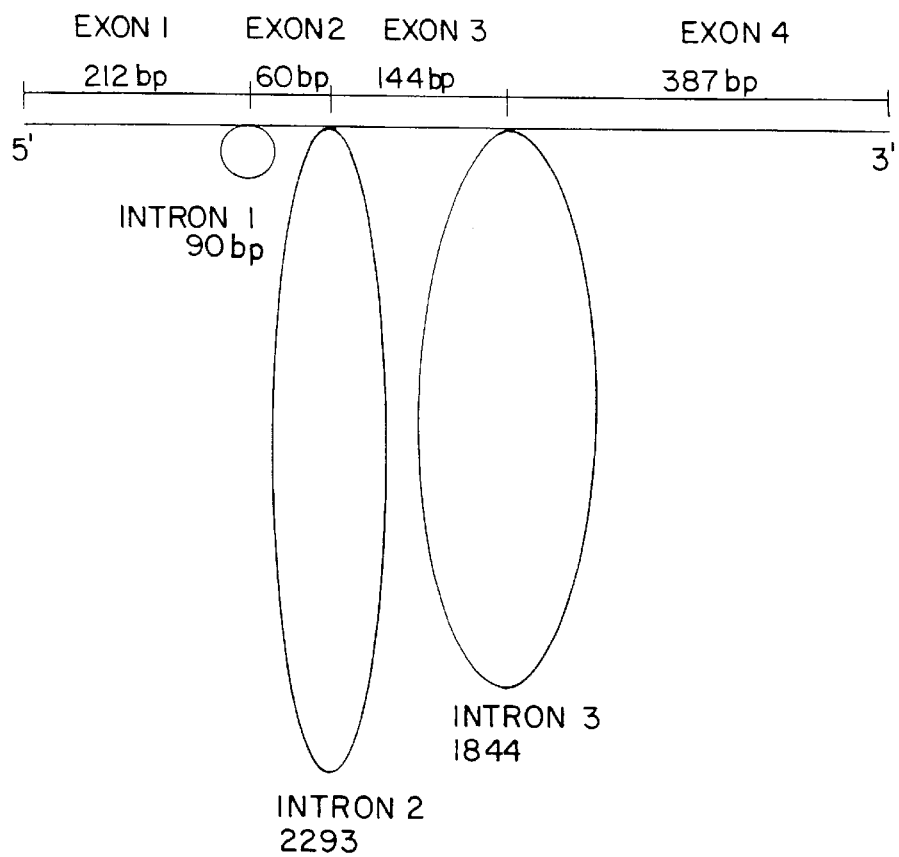
FIG. 1 is a schematic representation of the intronlexon structure for the IL-2 gene.
Figure 2:
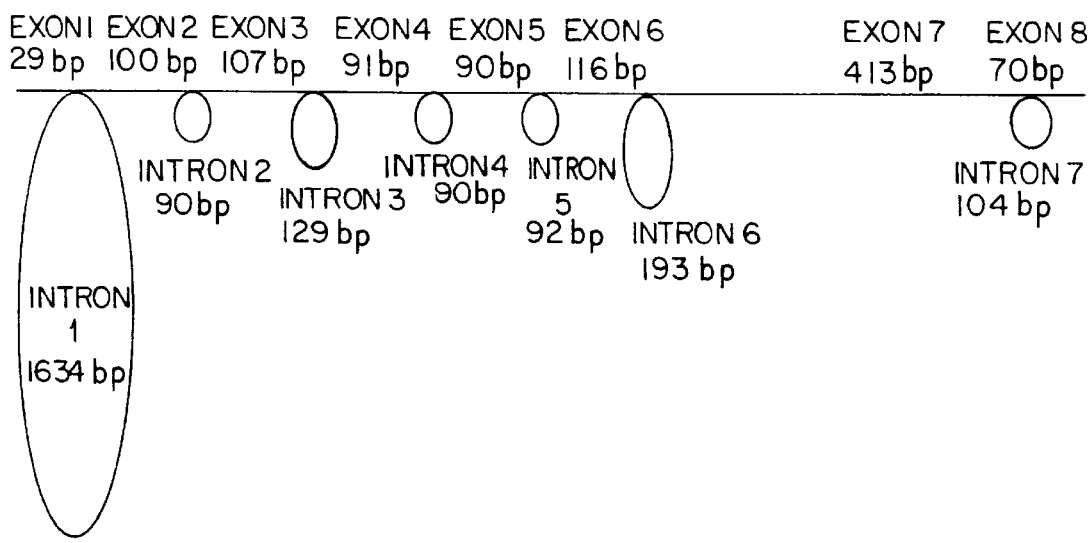
FIG. 2 is a schematic representation of the intron/exon structure for the GAPDH gene.

The instant invention describes a method for quantitatively measuring the level of transcription of specific genes in biological specimens. Gene expression that may be determined according to the present invention is that of any transcribed gene in which both the RNA and DNA sequences have been characterized and which contain sequence heterogeneity between the DNA and the mRNA. By way of illustration, included herein is the exon/intron characteristics of the human IL-2 gene (FIG. 1) or GAPDH gene (FIG. 2).

Figure 4:
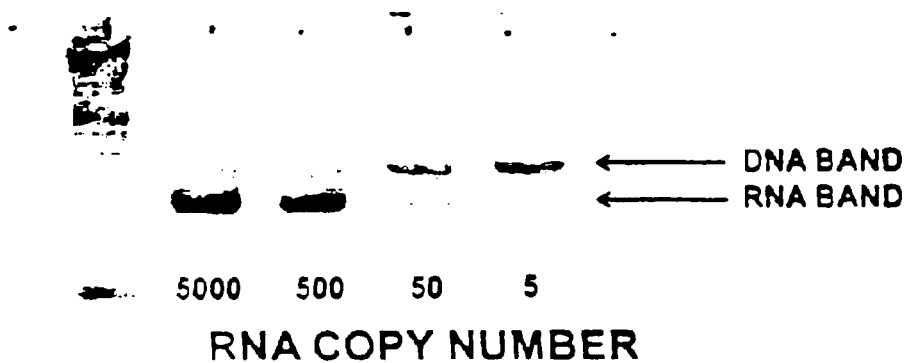
FIG. 4 shows an agarose gel electrophoretogram exhibiting DNA and RNA banding patterns following a PCR titration of mRNA to a constant DNA concentration.

In one embodiment, the present invention specifies the duplex amplification, preferably with a single set of primers, capable of amplifying both genomic DNA and expressed mRNA from the same gene sequence, thereby competitive PCR quantitation based upon changes in ratio of mRNA to genomic DNA. In an embodiment of the invention, relative copy numbers of mRNA and DNA are determined by separating the amplimers by size and measuring or estimating their relative amounts. Since the DNA amplimer is longer than the mRNA amplimer, gel electrophoresis or other size-discriminating chromatography separates them, (FIG. 4). Each amplimer is visualized and quantified by autoradiography, radiographic counting, densitometry, or any such technique. In other embodiments of the invention, relative copy numbers of the mRNA and DNA are determined by using hybridization/detection probes. For example, one, probe is preferably, specific to the intron sequences of the DNA, and another, probe is preferably, hybridized exclusively to only mRNA at the splice junction (see, FIG. 11). These probes are then used to allow measurements of the DNA to mRNA amplimer ratios. Examples are two such probes designed for use with the IL-2 detection system. The sequences of interleukin 2 capture probe sequences for use with the primer sequences disclosed in Table I are provided in Table II. Selective label reporters A and B may be fluorescent label, antibody hapten, electrochemiluminescence label, bioluminescence label, chemiluminescence label or any enzyme label standardly used for ELISA assays. Selective labeling of the detection probes allows their use in a variety of detection technologies, for example, fluorescence detection, electrochemiluminescence detection, chemiluminescence detection, bioluminescence detection and enzyme-linked immunosorbent detection (ELISA).

Figure 12:
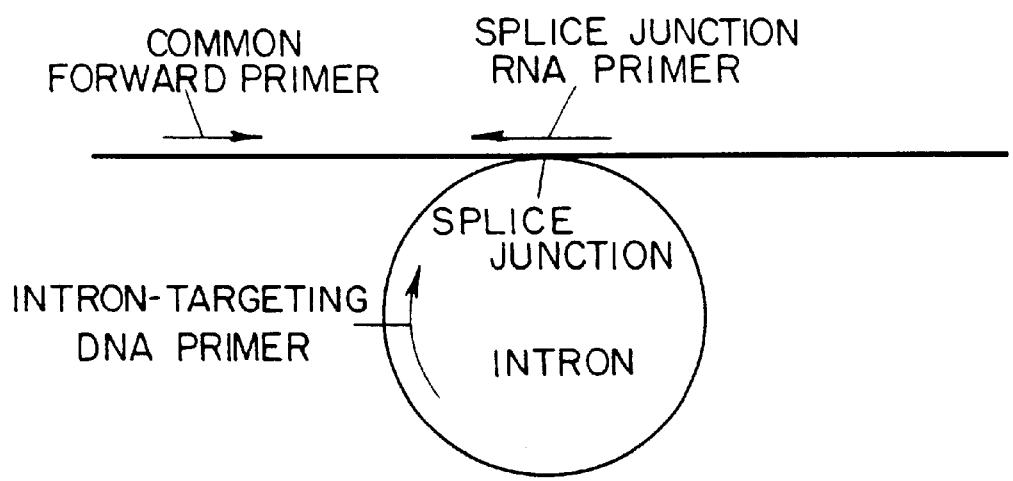
FIG. 12 illustrates a common primer and two downstream primers used for amplification and discrimination.

In an alternate embodiment, only one common hybridization primer for amplification is used. In place of the second amplification primer and two distinct detection probes, two distinct primer/detection probes are used (see for example FIG. 12). In this way, the DNA amplimer is defined by the common primer and the second amplification primer binding to the intron. The mRNA amplimer is defined by the common primer and its second amplification primer binding to the splice junction sequence. The DNA and mRNA specific primers act as combination amplification primers and detection probes and are labeled for this purpose. This embodiment is most useful when only very large introns are present in the DNA for the gene. Flanking much larger introns with two common primers can be problematic with current amplification technologies. Removing the requirement for two common primers allows freedom in determining the amplimer length, independent of intron size.

Another alternate embodiment provides a transcription region primer pair designed to amplify both the RNA and DNA material. This embodiment is useful for quantitation of gene expression when no introns are present in the RNA transcription region.

In another embodiment of the invention, the level of transcription of a specific gene is quantitatively measured by: a) nucleic acid extraction; b) primer and probe sequence design; c) polymerase chain reaction; and d) quantitative gene expression determination.

An additional embodiment uses the ratio of genomic material to expressed mRNA, as measured by any complementary DNA, RNA or PNA probe binding to the genomic material and mRNA to determine gene expression. This may be accomplished without prior amplification of the genomic material or mRNA.

One skilled in the art recognizes that quantitation, as disclosed herein, may be performed in a broad range of biological samples. Such samples include, for example, biological samples derived from agriculture sources, bacterial and viral sources, and from human or other animal sources, as well as other samples such as waste or drinking water, agricultural products, processed foodstuff and air. More specifically, samples include, for example, blood, stool, sputum, mucus, serum, urine, saliva, teardrop, biopsy samples, histological tissue samples, tissue culture product, an agricultural product, waste or drinking water, foodstuff and air. The present invention is useful for the quantitation of RNA transcripts indicative of specific gene expression in any sample containing nucleic acid.

Various terms are used in this specification, for which it may be helpful to have definitions. These are provided herein, and should be borne in mind when these terms are used in the following examples and throughout the instant application.

As used herein, the term "amplification" refers to a template-dependent process by which multiple copies of nucleic acid sequences are formed, resulting in an increase in the concentration of a nucleic acid sequence relative to its initial concentration.

As used in this invention, a "template-dependent process" is defined as a process that involves the template-dependent extension of a primer molecule. A template-dependent extension refers to nucleic acid synthesis of RNA or DNA wherein the sequence of the newly synthesized strand of nucleic acid is dictated by the rules of complementary base pairing of the target nucleic acid and the primers.

A "primer" molecule refers to a nucleic acid sequence, complementary to a known portion of the target sequence/control sequence, necessary to initiate synthesis by DNA polymerase. A short primer sequence base-paired to a specific site, for example, an intron, on a longer nucleic acid can initiate polymerization from that site. As used in this invention, a "common intron primer" is defined as a primer sequence that is identical for different targets, i.e., they have the same primer sequences in common. Further, a "composite primer" as used herein, refers to a primer including a hybrid with a portion of the sequence complementary to the target, and the remainder non-complimentary. During the PCR reaction the polymerase copies through the non-complimentary sequence resulting in its incorporation into the target. Generally, primers are molecules that serve as the initiator of amplification.

A "probe" is a molecule that is capable of binding a reporter to native RNA or DNA or their amplification products and is designed to bind to the portion of the RNA or DNA that is different in sequence or length. In other words, a probe is a molecule that is capable of delivering a reporter molecule specifically to either the RNA or DNA by binding to the portion of the sequence that is different between them. Probes may be composed of nucleic acid, protein, or any molecule capable of binding to a unique sequence. When composed of nucleic acid, probes may function as primers. A probe is a vehicle for attaching a reporter molecule to another molecule.

"Competitive PCR" refers to amplification reactions wherein the control fragment and the target utilize the same primer sequences resulting in competition of the primers for the target and the control fragment. "Target nucleic acid sequence" refers to the nucleic acid molecule that is to be amplified. The target molecule can be present in a purified, partially purified or unpurified state in the sample.

"Control fragment" is defined as a nucleic acid sequence utilized as a standard in quantitation. "Internal fragment" is the nucleic acid present in each individual PCR reaction that can be utilized as a control.

As used herein, "amplification competitor" refers to a nucleic acid containing the same primer recognition sequences as the target nucleic acid molecule.

"Amplimer" is a term of art, known to and understood by the skilled artisan, as referencing the nucleic acid amplification product. "Sequence heterogeneity discrimination" means that the sequence of the RNA or its amplification product is different than the sequence of the DNA or its amplification product, and that this difference can be detected, or measured, or identified. The instant method takes advantage of the sequence differences between RNA and DNA. That is to say, detecting the sequence differences between two difference nucleic acid molecules. Numerous methods are known and used in the art to discriminate and/or determine sequences.

"Constitutive gene expression" means that the genes are expressed in all cells at relatively constant levels and are not regulated or induced.

This application uses "signal cross-talk" to refer to the degree of specificity as measured by the detection signal of two different probes.

The present invention is embodied in a method for the quantitative determination of gene expression, particularly useful for small tissue samples. Regardless of the specific application of the instant invention, the methodology details are calculated according to protocols well known in the art, as well as those disclosed herein. Further, the refinement of said necessary calculations is routinely made by those of ordinary skill in the art and is within the ambit of tasks routinely performed by them without undue experimentation.

One embodiment of the present invention is a method of quantitatively measuring the level of transcription of specific genes in biological specimens, said method comprised of the following steps:

a) extracting from any biological specimen the nucleic acid in such a manner such that both the DNA and RNA are obtained in a consistent yield ratio;

b) designing primer and probe sequence for performing amplification reactions in such a manner that both the messenger RNA and DNA are amplified by means of the same primer recognition sequences;

c) performing amplification, such as by PCR, utilizing a single tube, one step reaction wherein the above primers and probes are included together with recombinant reverse transcriptase enzyme in such a manner as to generate distinguishable fluorescent signals specific to RNA or DNA by means of a homogeneous nuclease reaction; and d) determining relative gene expression through multiplex componenting the ratio of the RNA to DNA fluorescent signals, or determining absolute RNA copy number relative to a standard curve derived by the ratio of known concentrations of purified RNA and DNA for the gene.

Figure 3:
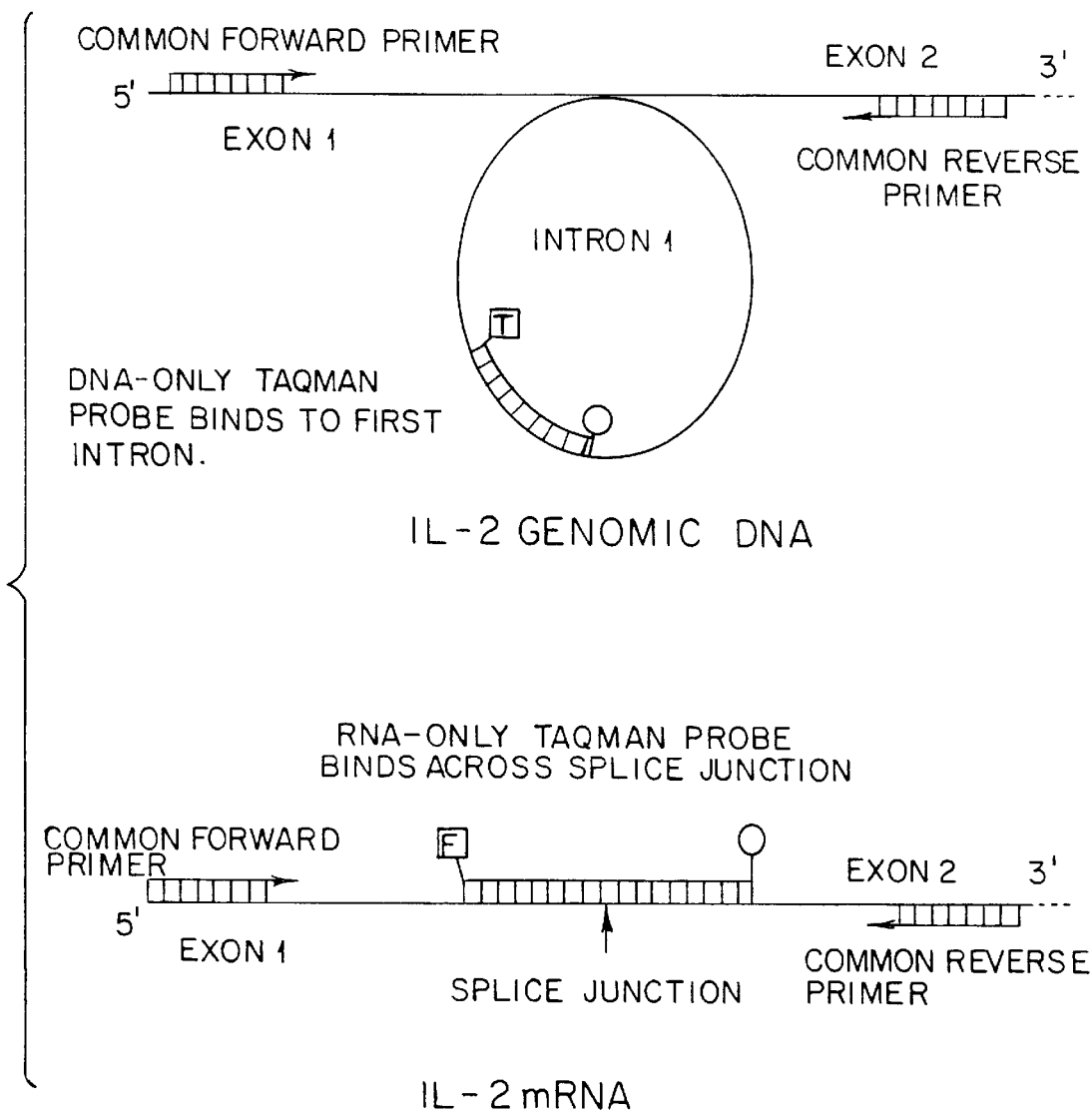
FIG. 3 depicts the strategy for primer and probe design.
Figure 11:
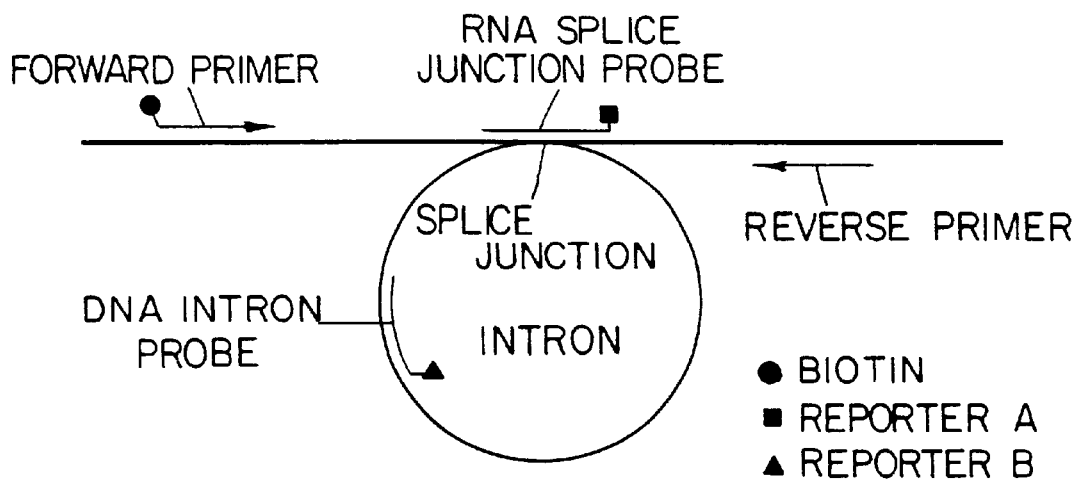
FIG. 11 represents a generic hybridization-capture probe scheme.

Primer and probe sequences are designed specifically for performing amplification reactions in such a manner that both the messenger RNA and DNA are amplified by means of the same primer recognition sequences (see FIG. 11). That is, said primers are designed so as to be complementary to sequence located within two exons flanking an intron of a size consistent with the amplification method capability. Alternatively, where the introns for a target gene all exceed the size readily amplified by the amplification technology of choice, one common primer is designed for both mRNA and DNA and complementary is in an exon adjacent to the intron. The second primer for DNA amplification is designed to be complementary to a sequence located in the intron sequence and the second primer for the mRNA amplification is designed to be complementary to the splice junction sequence for that intron. In this case, the second primers simultaneously serve as detection probes (see FIG. 12). In all cases, the probes are labeled with reporter molecules or haptens to facilitate their detection. An illustrative example of the method is the use of PCR as the amplification technique and TaqMan® probes for detection. The TaqMan® probes are bifunctionally tagged with fluorophores so as to be self-quenching. The two probes are further designed so that one probe with reporter fluorescent tag A specifically hybridizes only within the DNA of the particular gene intron, while the second probe with reporter fluorescent tag B specifically hybridizes only to the splice junction of the messenger RNA for the same gene. Probe and primer design is illustrated in FIG. 3.

The method disclosed and taught herein is applicable not only to the preferred PCR-based embodiment, as discussed above, but also to any and all other amplification methods, wherein the amplification of both DNA and RNA is provided in a competitive reaction and/or detection probes are designed to measure DNA intron sequences relative to mRNA sequences at the splice junction.

Another embodiment, for example, is the use of gap filling ligase chain reactions (see, U.S. Pat. No. 5,427,930 to Birkenmeyer et al., which is specifically incorporated herein by reference). In a ligase application, one set of ligation probes is designed to be specific to DNA intron sequences, while a second duplex set in the same reaction is designed to be specific to the mRNA splice junction. Following ligase chain reaction amplification with all probes included within one reaction tube, the detection step is split into two tubes each developed for different reporter haptens in the established LCx format.

The present invention further includes methodologies for quantitatively measuring the level of transcription of specific genes in biological specimens without the use of amplification and/or primer binding.

Due to its simplicity, specificity for transcription, and high sensitivity, this aspect of the invention enables transcription to be more reliably and readily measured. In particularly, this invention is applicable to small tissue samples, for example, fine needle biopsies of tumors or transplanted organs, amniotic fluid sampling, atherosclerotic tissue, and other biological specimens previously requiring invasive procedures to obtain adequate material for measuring specific gene transcription. The instant invention is readily amenable to commercialization in the biology, biomedical research, and clinical diagnostic arenas, for example, in the form of kits including primer sets and corresponding detection probes for the gene of interest.

Those skilled in the art will readily recognize the present invention is broadly applicable to any transcribed gene in which both the RNA and DNA sequences have been characterized and in which there is sequence heterogeneity between the RNA and the DNA. The following examples serve to explain and illustrate the present invention. Said examples are not to be construed as limiting of the invention in anyway. Various modifications are possible within the scope of the invention.

EXAMPLE 1

PCR Probe and Primer Design

Primers and probes are designed as outlined in FIG. 3 and Table I. The primers amplify both RNA and DNA in the same reaction by means of the same primer sequences. The probes are "TaqMan®" probes specific to the DNA intron or the splice junction of the RNA. PCR primer and "Taq-Man®" probes are designed for both the Human IL-2 gene and the Human GAPDH genes (see, FIGS. 1 and 2 respectively). PCR primers flanking the, small IL-2 intron were designed and subsequently purchased from Operon Technologies (Alameda, Calif.). Two "TaqMan®" probes for the IL-2 gene, one for binding to the intron for DNA detection and the other for binding across the splice junction for RNA detection, were designed and subsequently ordered from Applied Biosystems Division of Perkin Elmer (Foster City, Calif.)(see, FIG. 1). The DNA-specific "TaqMan®" probe was made with a different reporter fluorophore from that used in the RNA probe. A similar set of PCR primers and "TaqMan®" probes were designed for use with the fourth intron in the GAPDH gene (see, FIG. 2).

EXAMPLE 2

Isolation of Nucleic Acid

A commercial rapid preparation, "QIAamp HCV", is utilized for the isolation and extraction of total nucleic acid per the manufacturer's instructions (Qiagen Inc., Chatsworth, Calif.). The method disclosed herein is compatible with any nucleic acid extraction methodology, wherein both DNA and RNA are purified.

EXAMPLE 3

Confirmation of Probe Specificity

The first set of experiments performed with the components of this assay were designed to confirm the lack of cross-talk between the DNA and RNA "TaqMan®" probes using RAJI cell DNA and RNA and the GAPDH gene probes. The results of these experiments confirm a lack of cross-talk, but only after retreating the pure RNA preparation with preparations from DNA contamination or vice versa. Simplex PCR (only one "TaqMan®" probe in a reaction) using purified DNA and RNA shows signal generation using RAJI cell DNA and RNA, respectively. Also, cross-talk is observed between the GAPDH gene DNA probe and the RAJI cell RNA preparation; cross-talk is not observed between the RNA probe and the RAJI cell DNA preparation. Further treatment of the RNA preparation with additional DNases eliminates this cross-talk. Similar experiments with the IL-2 "TaqMan®" probes give similar results, not shown here.

EXAMPLE 4

GAPDH Constitutive Transcription/IL-2 Induction

Jurkat cells, American Type Culture Collection No. T1B-152 clone E6-1 (ATCC E6-1), are grown to the desired cell density and split up into 1.0 ml cultures. Mitogen is added to these in 0×, 1×, 5× and 10× concentrations and the cultures returned to the incubator and harvested at the following times: 2 hours, 4 hours, 8 hours, 24 hours, 48 hours and 72 hours subsequent to mitogen addition. The total nucleic acid is extracted and purified using "QIAamp" columns and stored frozen, at −20° C. (Qiagen Inc., Chatsworth, Calif.). "TaqMan®" PCR with nucleic acid preparations from Jurkat cells give signal for both the DNA and RNA GAPDH, and the IL-2 DNA probes.

IL-2 induction is performed using Jurkat cells grown to a density of $2\times10^6$ cells per milliliter with phytohemagglutinin and phorbol myristate acetate as mitogens (1.0 µg/ul and 50 µg/ul, respectively). The cells are harvested at various time points following mitogen addition with a no-mitogen control at each time point. Total nucleic acid is extracted using a "QIAamp HCV" kit (Qiagen Inc., Chatsworth, Calif.). For both RNA and DNA amplification via PCR, the Perkin Elmer "GeneAmp EZ" rTth RNA PCR kit is used (Perkin Elmer Corp., Foster City, Calif.). PCR conditions are as follows: each 50 µl reaction is done in 1×EZ RT buffer; 25 mM Mg(OAC)$_2$; 300 µM each dNTP; 500 nM each PCR primer; 100 nM each "TaqMan®" probe; and 0.1 units/?L rTth DNA polymerase. Nucleic acid from each cell extraction is used as template in a concentration of 1 to 5 µg/50 µl PCR reaction. Cycling conditions are: 15 minutes at 60° C. for RT; followed by 50 cycles of 15 seconds at 94° C. melt and 1.0 minute at 55° C. for anneal/extend. After PCR the samples are cooled to 4° C. and transferred to a Perkin-Elmer "Hi-White" microtiter plate. Fluorescence detection is done using a Perkin-Elmer LS-50B fluorescence spectrometer with microplate reader attachment (Perkin Elmer Corp., Foster City, Calif. ). Multi-componenting analysis and all subsequent calculations are performed by computer, using Microsoft "Excel" (Microsoft Corp.). The ratio of the RNA signal divided by the DNA signal for each sample is plotted against the amount of time following mitogen addition. To check for cross-talk between the DNA and RNA "TaqMan®" probes, purified DNA and RNA preparations from RAJI cell lines are used in simplex PCR. The RAJI nucleic acid preparations were the kind gift of Paul Wyatt of the Applied Biosystems Division of the Perkin Elmer Corporation.

Figure 5:
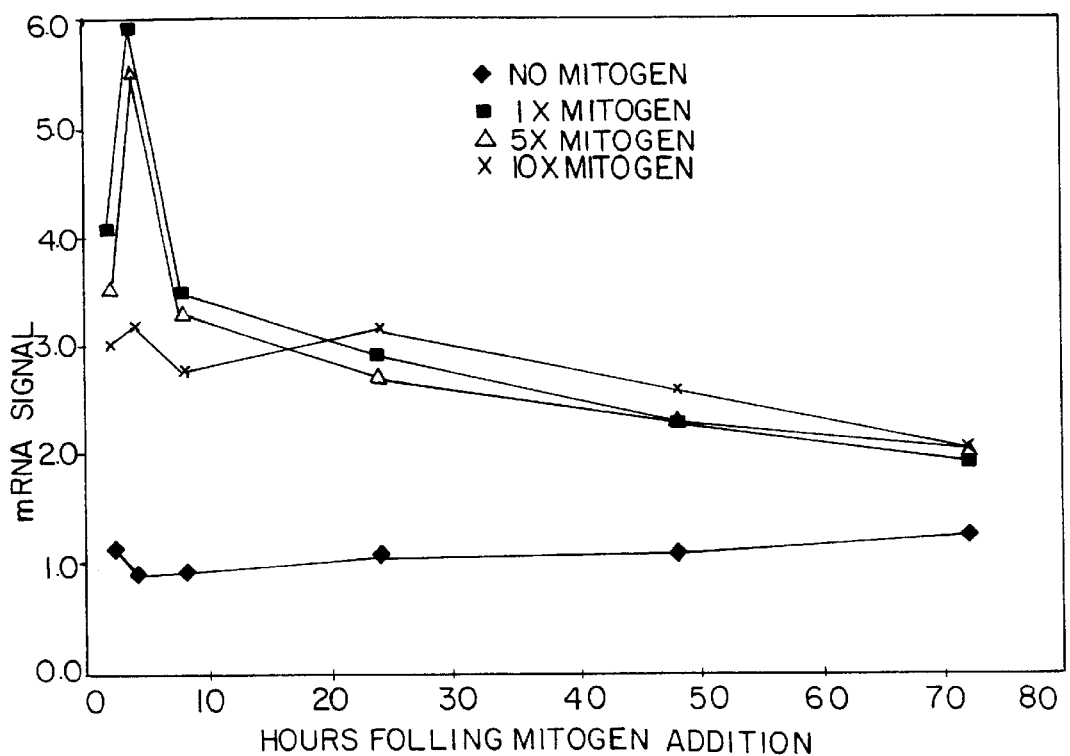
FIG. 5 shows the RNA IL-2 probe signal using only an RNA probe only in amplification reactions at various time intervals following induction of Jurkat cells.
Figure 6:
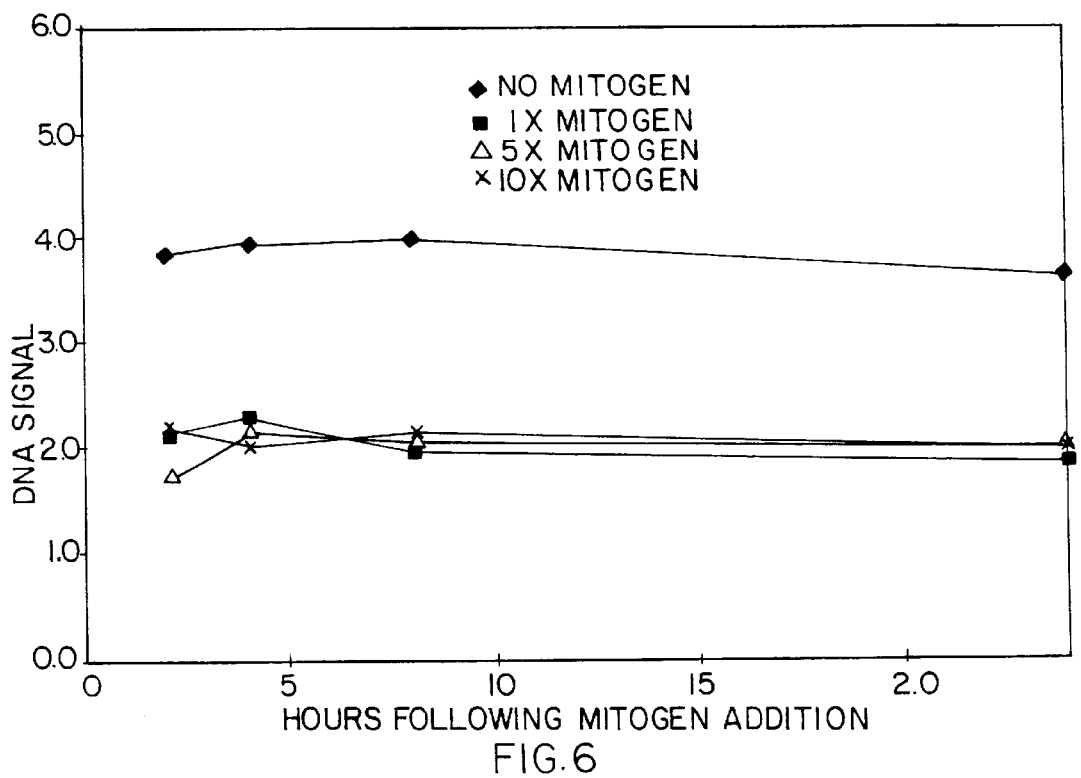
FIG. 6 is the DNA IL-2 probe signal using only a DNA probe in amplification reactions at various time intervals following induction of Jurkat cells.
Figure 7:
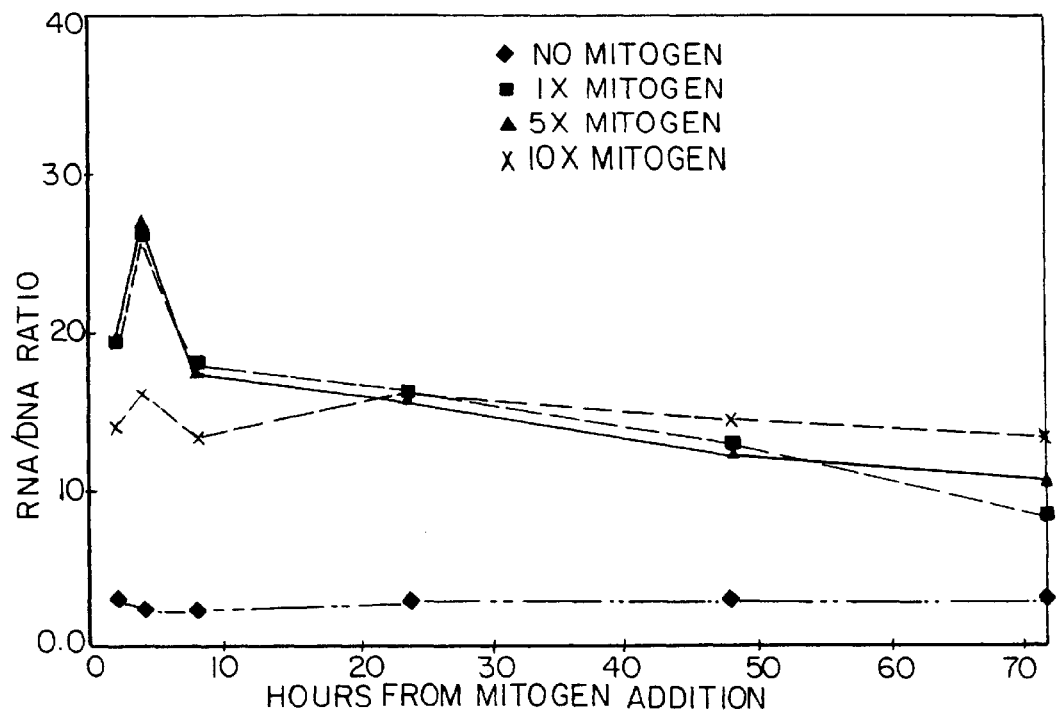
FIG. 7 displays the data of FIGS. 5 and 6 as the ratio of the RNA to DNA ratios at each time point.
Figure 8:
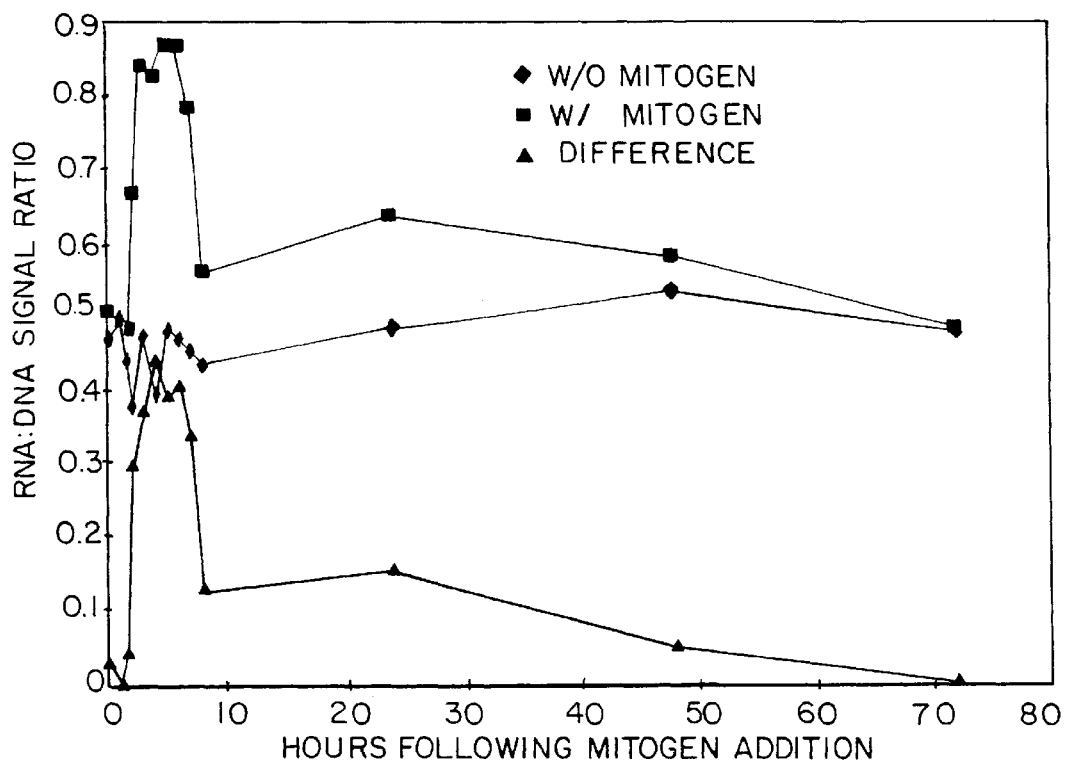
FIG. 8 depicts the IL-2 RNA to DNA ratios observed when both probes are present in the same amplification reactions at various time intervals following induction of Jurkat cells.

Signal from the IL-2 RNA probe is only seen from cells grown in the presence of the mitogen. For the IL-2 assays, the first PCR reactions are simplex reactions having either the RNA probe or the DNA probe. The signal from each probe is plotted against time for each level of mitogen addition (see, FIGS. 5 and 6). From this data, the ratio of the RNA signals to the DNA signal at the same time points calculated at each time point and plotted in FIG. 7. Following this, a similar assay is set up in which both DNA and RNA probes are present in each reaction. The plots of the RNA/DNA ratios against time are shown in FIG. 8.

Figure 9:
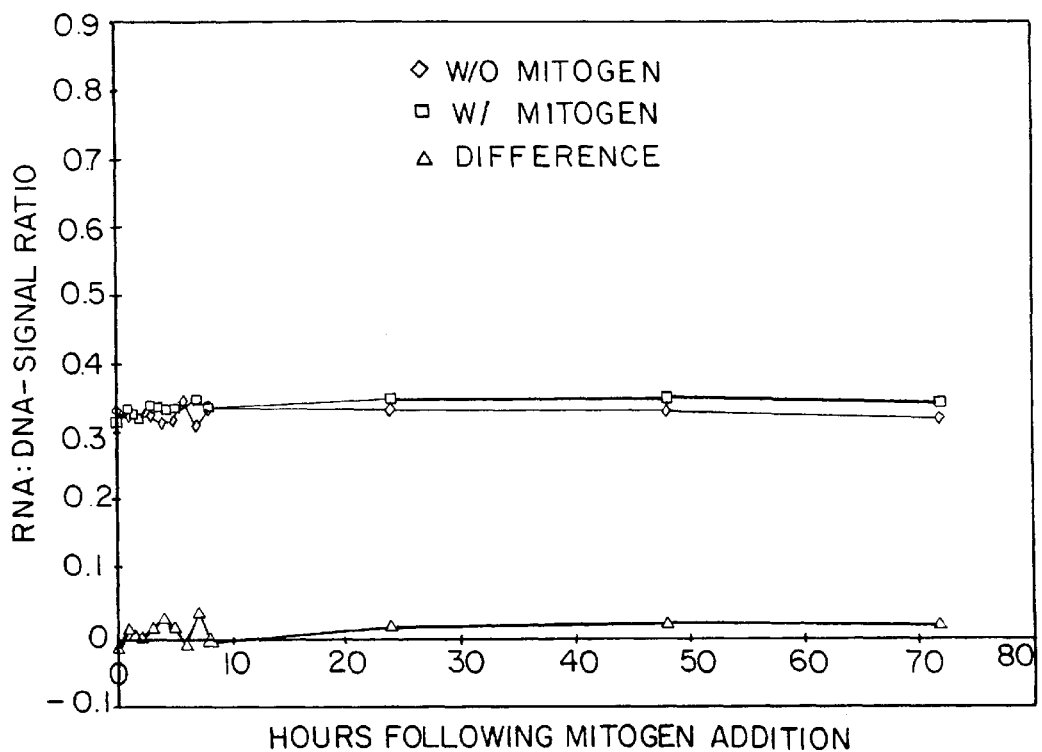
FIG. 9 depicts the GAPDH RNA to DNA ratios observed when both probes are present in the same amplification reactions at various time intervals following induction of Jurkat cells.
Figure 10:
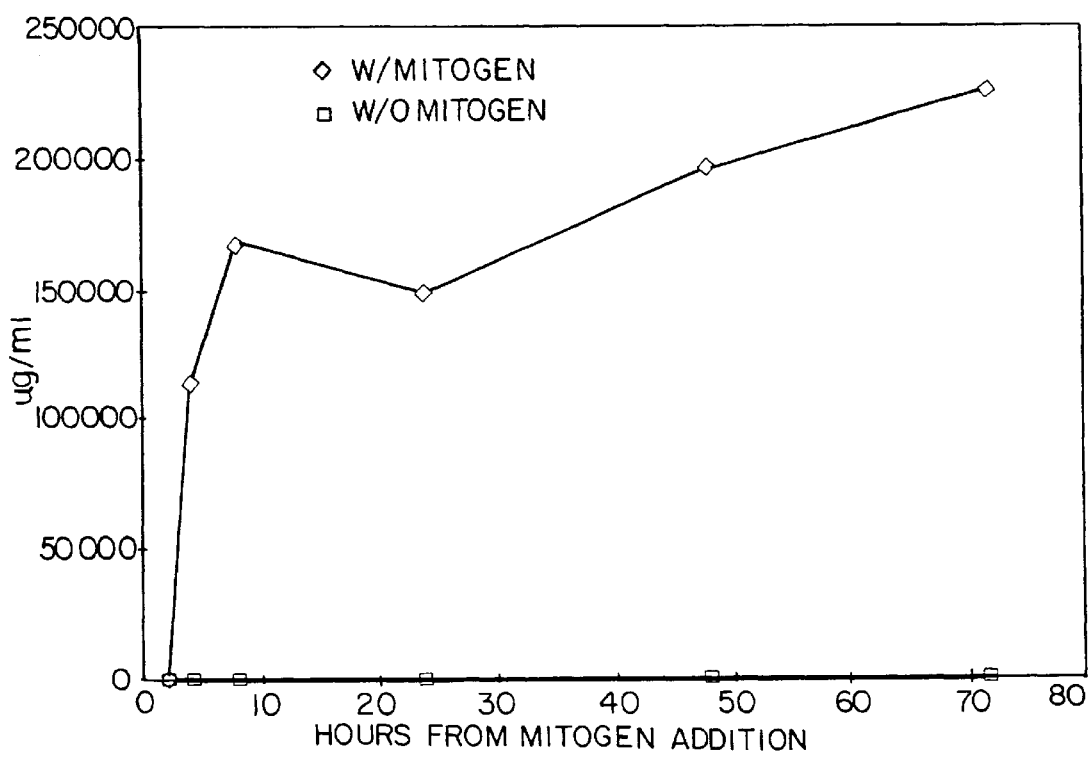
FIG. 10 depicts the IL-2 protein detectable by means of an ELISA reaction at various time intervals following induction of Jurkat cells.

Multiplex PCR with both GAPDH probes is carried out with all of the same samples, as indicated in the above-disclosed simplex PCR, and the results are plotted in a similar fashion as well (see, FIG. 9). From each of the figures presented herein, it is apparent that the IL-2 mRNA is expressed only in the presence of mitogen, and is expressed early. The amount of IL-2 DNA is relatively constant, showing some variation at the early time points. This may be due to differences in cell density following mitogen addition. The effect of mitogen on cell growth and density is discussed below. Examination of the ratio of RNA to DNA, both in the graph showing the ratios of the simplex data (FIG. 7) and the graph of the duplex data (FIG. 8), clearly shows the increase in IL-2 mRNA following induction. The specificity of the IL-2 induction was verified by assay of all cell supernates for IL-2 protein using the "Predicta®" IL-2 kit (Genzyme Diagnostics, Cambridge, Mass.). The amount of GAPDH mRNA relative to DNA is largely constant. It is observed, from the simplex IL-2 DNA data (FIG. 10), that clearly the absolute amount of DNA in the cells that did not have mitogen added is greater than that amount of DNA in the cells receiving mitogen. Close examination of the cell cultures shows that in the presence of mitogen there is significant cell-mortality, up to 50%. The DNA data show that this system detects absolute changes in nucleic acid concentration when the DNA and RNA data are examined alone. In spite of the large pparent difference in absolute amounts of nucleic acid present in the various samples, the ratio of the RNA signal to the DNA signal is insensitive to absolute amounts of nucleic acid, but is sensitive to changes in the ratio of mRNA to DNA. Since both nucleic acid extraction procedures and PCR can vary in efficiency, a system that is insensitive to absolute levels of nucleic acid and sensitive to changes in the mRNA to DNA ratio for a given gene is of great value. This simple, yet powerful, approach clearly accomplishes this goal and promises to have great utility for gene expression studies in a large variety of systems.

EXAMPLE 5

Size Discrimination Amplimer Detection

Any technique that detects and/or quantifies nucleic acids based upon size or sequence discrimination, for example gel electrophoresis, hybridization capture and TaqMan® PCR, respectively, is suitable for amplimer detection with this invention. The simplest such methodology is agarose gel electrophoresis. This technique is dependent upon the tendency for nucleic acids, which have a net negative charge in solution, to migrate towards the positive pole in an electric field. That is to say, the resulting amplimers from the reaction migrate towards the positive pole. The gel matrix physically retards the flow of the nucleic acid, therefore, shorter molecules migrate more quickly than longer ones. Hence, separation of a mixture of nucleic acids based upon size occurs and the various sizes of nucleic acids form bands of material comprised of similarly sized molecules. DNA amplimers formed by the process comprising this invention are longer than the RNA amplimers formed, and thus, migrate more slowly in this type of gel electrophoresis. A typical result is two discreet bands of material; the DNA amplimers and the mRNA amplimers.

A model PCR experiment using the primers for the GAPDH gene, intron 4, was performed. In this experiment, the amount of input purified genomic DNA is used for the DNA template (provided by Dr. Paul Wyatt). Purified human poly A mRNA, assayed for GAPDH mRNA, is used for the mRNA template. This often used preparation of messenger RNAs is purified by virtue of the presence of long homopolymeric runs of Adenosine bases added to mRNAs in eukaryotic organisms. The amount of GAPDH mRNA and genomic GAPDH DNA in each template had been carefully quantified by limiting dilution PCR. Four PCR reactions are set up in which the GAPDH DNA is held constant at 25 copies and the GAPDH mRNA is varied at 5, 50, 500 and 5000 copies of input template. After 40 cycles of PCR amplification (reaction conditions identical to those described supra, sans TaqMan® probe), aliquots of each reaction are placed in loading buffer and run on a 3% agarose gel at 125 volts constant current for 15 minutes, standard electrophoresis conditions. The agarose gel is prepared with ethidium bromide (EtBr) for band visualization. The resultant gel is shown in FIG. 4 in which the DNA band is clearly distinguishable from the RNA band. The relative band intensities exhibited in the gel clearly reflect the ratio of input RNA to DNA changes. While simple visualization of the amplimers in gel electrophoretograms is somewhat crude, more precise gel-electrophoresis quantitation methodologies may be used to actually quantify the intensities of the bands. The instant gel serves to illustrate the ease with which the DNA amplimers are distinguished from the RNA amplimers on the basis of size, while the above TaqMan fluorescent signal example illustrates discrimination by sequence.

EXAMPLE 6

Quantitative Measurement Without Prior Amplification

An alternative assay for quantitative measurement of transcription level of specific genes uses the ratio of genomic material to expressed mRNA. Said ratio is measured by any complementary DNA, RNA or PNA probe binding to the genomic material and mRNA that discriminates between the genomic material and mRNA by sequence heterogeneity without nucleic acid amplification and/or primer binding, for example, the independent detection of the genomic material and the mRNA by complementary probe binding where the probe is detected directly without prior amplification of the genomic material and mRNA. Said detection is accomplished by signal amplification methodologies or sensitive direct detection of the bound probe.

EXAMPLE 7

Quantitative Measurement Without RNA Transcription Region Introns

Occasionally, situations arise where the common primers cannot flank both the DNA and the RNA sequence heterogeneities. An example of this situation is a gene having no introns in the RNA transcription region. In this case, a primer pair is designed in the transcription region that amplifies both the RNA and the DNA materials. A flanking primer is designed to bind in an upstream or downstream region of the gene that is not included in the RNA transcript may be used with one of the transcription region primers. For example, a forward-sense primer in an upstream promoter region would function with a reverse-sense primer in the transcript region, and only amplify the DNA. The reverse-sense primer would then function with both forward sense primers, the one in the transcript region and the one in the promoter, or non-transcript, region. This primer then satisfies the requirement for a common, competitive amplification primer. The resulting amplification products correspond to DNA only amplification and DNA plus RNA amplification. Changes in gene transcription rates are reflected in changes in the (RNA+DNA)/DNA only amplification product ratios.

Figure 13:
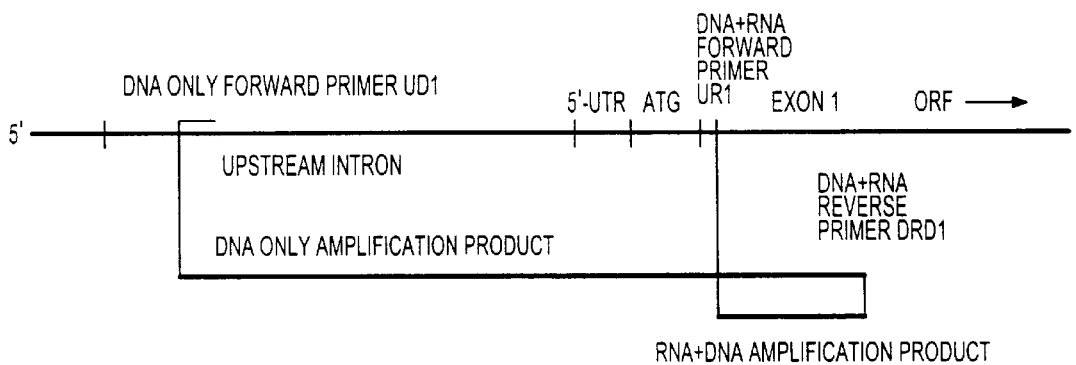
FIG. 13 illustrates gene expression quantitation primer design for the Estrogen Receptor gene.

This embodiment of the invention employing the Estrogen Receptor gene is diagramed in FIG. 13. Competitive amplification is attained through the use of a common downstream reverse primer (DRD1), located in Exon 1, and which is complementary to a sequence in the mRNA transcript. Two forward primers are then employed. The first, UR1, is located in the Exon 1 and is also included in the mRNA transcript. The specific sequences of each of the above primers is disclosed in Table III. Amplification with this primer pair results from both genomic DNA and mRNA as targets. The second forward primer, UD 1, is complementary to a sequence in the intron upstream of the transcription start site. Amplification with this forward primer and the common reverse primer, DRD1, occurs only with genomic DNA as the template. The two amplification products may be distinguished either by size or by design of probes directed to recognize the sequence differences, or by any of the detection methodologies discussed herein. The Estrogen Receptor gene expression rates are reflected by changes in the ratio of the UR1–DRD1 products/ UD1–DRD1 products (RNA+DNA)/DNA only).

Thus, the instant invention includes any detection of genomic material and the mRNA that relies upon detection either by a sequence difference, with or without the use of amplification of the nucleic acids and/or with or without the use of primer binding, or detection by a size difference with or without the use of amplification of the nucleic acids.

While the above description contains many specificities, these specificities should not be construed as limitations on the scope of the invention, but rather exemplification of the preferred embodiment thereof. That is to say, the foregoing description of the invention is exemplary for purposes of illustration and explanation. Without departing from the spirit and scope of this invention, one skilled in the art can make various changes and modifications to the invention to adapt it to various usages and conditions. As such, these changes and modifications are properly, equitably, and intended to be within the full range of equivalence of the following claims. Thus, the scope of the invention should be determined by the appended claims and their legal equivalents, rather than by the examples provided herein.

TABLE I

INTERLEUKIN 2 PRIMER AND PROBE SEQUENCES
PCR PRIMERS
  FORWARD PRIMER (IL-2 Forward )
  bp: 313–329
    5'-GTCTTGCATTGCACTAA                           SEQ ID NO:1

REVERSE PRIMER (IL-2 Reverse)
    5'-TAAATGTGAGCATCCTG                           SEQ ID NO:2

RNA TAQMAN ® PROBE
  (SPLICE-JUNCTION PROBE) bp-mRNA: 203–233
    5'-R-TTGGGATTCTTGTAATTATTAATTCCATT-Q           SEQ ID NO:3

DNA TAQMAN ® PROBE (INTRON PROBE)
    5'-R-TTGCACTTGTCACAAACAGTGCACCT-Q              SEQ ID NO:4

GAPDH PRIMER AND PROBE SEQUENCES
INTRON 2
PCR PRIMERS
  FORWARD GFP12 bp: 2457–2474
    5'-GTTATTGGGCGCCTGGTC                          SEQ ID NO:5

REVERSE GRP12 bp: 3399–3417
    5'-CGCTCCTGGAAGATGGTGA                         SEQ ID NO:6

RNA SPLICE JUNCTION PROBE
GDRTPIN2 bp-mRNA: 174–203
    5'-R-TGACCTCAACTACATGGTTTACATGTTCCA-Q          SEQ ID NO:7

DNA INTRON PROBE
GDTPINT2 bp: 3274–3300
    5'-R-CAGCCCCTTCATACCCTCACGTATTCC-Q             SEQ ID NO:8

INTRON 4
PCR PRIMERS
  FORWARD GFP14 bp: 3575–3593
    5'-TGGCGCTGAGTACGTCGTG                         SEQ ID NO:9

TABLE I-continued

REVERSE GRP14 bp: 3770–3789
    5'-ACATGGGGGCATCAGCAGAG                        SEQ ID NO:10

RNA SPLICE JUNCTION PROBE
GDTPINT4 bp-mRNA: 373–396
    5'-R-ATGGAGAAGGCTGGGGCTCATTTG-Q                SEQ ID NO:11

DNA INTRON PROBE
GRTPINT4 bp: 3662–3696
    5'-R-AGCTGACTCAGCCCTGCAAAGGCA-Q                SEQ ID NO:12

*R = Reporter Dye
*Q = Quencher Dye

TABLE II

INTERLEUKIN 2 CAPTURE PROBE SEQUENCES
  mRNA SPLICE JUNCTION CAPTURE PROBE bp: 182–205
    5'-TTATTAATTCCATTCAAAATCATC-Reporter A         SEQ ID NO:13

INTRON SEQUENCE CAPTURE PROBE bp: 488–511
    5'-TGTTATTAAGAAATGATCTCCAGC-Reporter B         SEQ ID NO:14

Reporter A and B can be:
  1. Fluorescent Label, such as:
     Fluorescein
     Fluorescein Isothiocyanate (FITC)
     Any fluorophore having an emission spectrum
     allowing spectral discrimination between
     reporter A and reporter B, for
     example, Fluorescein and Texan Red pair
  2. Antibody hapten, such as:
     Dinitrophenol (DNP)
     Digoxigenin
     Any hapten for which a specific antibody
     is available
  3. Electrochemiluminescence label, such as:
     Ruthenium label
     Any electrochemiluminescent label
  4. Bioluminescence label, such as:
     Aquorin
     Any bioluminescent label
  5. Chemiluminescence label, such as:
     Lumiphos
     Any chemiluminescent label
  6. Enzyme label, such as:
     Any used for standard ELISA assays

TABLE III

ESTROGEN RECEPTOR GENE PRIMERS
  UR1  Forward Primer, DNA and RNA
       "ER-FP-R"
         5'-CGCCGGTTTCTGAGCCTTCTG             SEQ ID NO:15

DRD1 Common Reverse Primer,
       DNA and RNA
       "ER-RP-C"
         5'-TGCTTTGGTGTGGAGGGTCAT             SEQ ID NO:16

UD1  Forward Primer, DNA only
       "ER-FP-D"
         5'-GCTGTCTGTGGCTGGCTGCGT             SEQ ID NO:17

What is claimed is:

1. A method for quantitation of gene expression which comprises:
   a) extracting nucleic acid from a biological specimen wherein said nucleic acid comprises mRNA transcripts and endogenous genomic DNA;
   b) designing complementary probe sequences specific for said mRNA transcripts and said endogenous genomic DNA, wherein said probe sequences discriminate between said endogenous geinomic DNA and said mRNA transcripts by sequence heterogeneity;
   c) hybridizing said complementary probe sequences to said mRNA transcripts and endogenous genomic DNA;
   d) directly detecting said endogenous genomic DNA and said mRNA transcripts; and
   e) quantitatively determining gene expression as expressed by the ratio of said mRNA transcripts to said endogenous genomic DNA.

2. The method as defined in claim 1, wherein direct detection of said endogenous genomic DNA and mRNA transcripts is accomplished via signal amplification methodologies or direct probe detection.

3. A method for quantitation of gene expression which comprises:
   a) extracting nucleic acid from a biological specimen, wherein said nucleic acid comprises mRNA transcripts and endogenous genomic DNA;
   b) designing sets of primer sequences specific for said mRNA transcripts and endogenous genomic DNA, wherein said sets of primer sequences include at least two primers which specifically hybridize to a coding region of said mRNA transcript and said endogenous genomic DNA, and wherein said sets of primers further include a primer which hybridizes to sequences of said endogenous genomic DNA but does not hybridize to sequences of said mRNA transcript;
   c) amplifying both said mRNA transcripts and endogenous genomic DNA using said primer sequences to produce mRNA amplimers and endogenous genomic DNA amplimers in a competitive reaction, said endogenous genomic DNA being a quantitation standard;
   d) detecting said mRNA transcript amplimers and said endogenous genomic DNA amplimers; and
   e) quantitatively determining gene expression as expressed by the ratio of mRNA transcripts to endogenous genomic DNA or as expressed by the ratio of mRNA transcript amplimers to endogenous genomic DNA amplimers.

4. The method as defined in claim 3, wherein said primers are labeled with detectable moieties.

5. The method as defined in claim 3 wherein said determination comprises the separation of said mRNA transcript amplimers and said endogenous genomic DNA amplimers by size.

6. The method as defined in claim 5 wherein said separation comprises chromatography.

7. The method as defined in claim 6, wherein said chromatography comprises gel electrophoresis, size-exclusion chromatography or high-performance liquid chromatography (HPLC).

8. The method as defined in claim 3, wherein said quantitation is determined by a change in gene transcription rate, wherein said change in gene transcription rate is expressed as the ratio of (mRNA amplimers plus endogenous genomic DNA amplimers) to endogenous genomic DNA amplimers.

9. The method as defined in claim 3, wherein the nucleic acid is the Estrogen Receptor gene having a transcription start site.

10. The method as defined in claim 9, wherein the primer sets comprise a common reverse primer that is complementary to a first sequence located in Exon 1 in the mRNA transcript, a first forward primer that is complementary to a second sequence located in Exon 1 in the mRNA transcript, and a second forward primer that is complementary to a sequence located in an intron upstream of the transcription start site.

11. The method of claim 3, wherein said primers include a first forward primer that is complementary to a sequence in said endogenous genomic DNA, a second forward primer that is complementary to a sequence in said mRNA transcript, and a common reverse primer, said reverse primer capable of amplifying both said mRNA transcript and said endogenous genomic DNA and acting as a competitive amplification primer.

12. The method of claim 3, wherein said detection comprises:
   a) designing complementary probe sequences specific for said mRNA amplimers and said endogenous genomic DNA amplimers;
   b) hybridizing said complementary probe sequences to said amplimers and said endogenous genomic DNA amplimers; and
   c) detecting said hybridized probes.

13. The method of claim 12, wherein said detection comprises fluorescence detection, electrochemiluminescence detection, chemiluminescence detection, bioluminescence detection and enzyme-lined immunosorbent assay (ELISA) detection.

* * * * *